United States Patent [19]

Williamson et al.

[11] Patent Number: 5,710,181
[45] Date of Patent: *Jan. 20, 1998

[54] INHIBITION OF NITRIC OXIDE FORMATION IN INFLAMMATORY BOWEL DISEASE

[75] Inventors: Joseph R. Williamson; John A. Corbett, both of St. Louis; Michael L. McDaniel, Glendale, all of Mo.; Ronald G. Tilton, Sugarland, Tex.

[73] Assignee: Washington University, St. Louis, Mo.

[*] Notice: The term of this patent shall not extend beyond the expiration date of Pat. Nos. 3,358,969 and 5,246,970.

[21] Appl. No.: 620,833

[22] Filed: Mar. 25, 1996

Related U.S. Application Data

[63] Continuation-in-part of Ser. No. 328,925, Oct. 25, 1994, abandoned, which is a continuation-in-part of Ser. No. 110,915, Aug. 24, 1993, Pat. No. 5,358,969, which is a continuation-in-part of Ser. No. 843,387, Feb. 28, 1992, Pat. No. 5,246,971, and a continuation-in-part of Ser. No. 906,632, Jun. 30, 1992, Pat. No. 5,246,970, which is a continuation-in-part of Ser. No. 807,912, Dec. 16, 1991, abandoned.

[51] Int. Cl.$^6$ .................................................. A61K 31/155
[52] U.S. Cl. ................................................................ 514/634
[58] Field of Search .................................................. 514/634

[56] References Cited

U.S. PATENT DOCUMENTS

| | | | |
|---|---|---|---|
| 3,541,218 | 11/1970 | Marshall et al. | |
| 4,758,583 | 7/1988 | Cerami et al. | 514/399 |
| 4,870,210 | 9/1989 | Musser . | |
| 5,128,360 | 7/1992 | Cerami et al. | |
| 5,246,970 | 9/1993 | Williamson et al. | 514/632 |
| 5,246,971 | 9/1993 | Williamson et al. | 514/634 |
| 5,273,875 | 12/1993 | Griffith . | |
| 5,317,040 | 5/1994 | Goldman et al. | |
| 5,358,969 | 10/1994 | Williamson et al. | 514/632 |

FOREIGN PATENT DOCUMENTS

| | | |
|---|---|---|
| 222313 | 5/1987 | European Pat. Off. . |
| 339496 | 2/1989 | European Pat. Off. . |
| 316852 | 5/1989 | European Pat. Off. . |
| 3206034 | 9/1991 | Japan . |

OTHER PUBLICATIONS

Southan et al. (1996), Selective Pharmacological Inhibition of Distinct Nitric Oxide Synthase Isoforms, *Biochemical Pharmacology* 51:383–94.

Corbett et al. (1993), Nitric Oxide Mediates IL-1β–Induced Islet Dysfunction And Destruction: Prevention By Dexamethasone, *Autoimmunity* 15:145–53.

Henrich (1990), Diabetes mellitus–ein Krankheitssyndrom und seine Behandlung, *Pharm. Ztg.* 135:1711–24.

Vlassara (1990), Chronic Diabetic Complications and Tissue Glycosylation Relevant Concern for Diabetes–Prone Black Population, *Diabetes Care* 13:1180–1185.

Bucala et al. (1991), Advanced Glycosylation Products Quench Nitric Oxide and Mediate Defective Endothelium-–Dependent Vasodilatation in Experimental Diabetes, *J. Clin. Invest.* 87:432–438.

Brownlee et al. (1986), Aminoguanidine Prevents Diabetes-–Induced Arterial Wall Protein Cross–Linking, *Science* 232:1629–1632.

Corbett et al. (1992), Does Nitric Oxide Mediate Autoimmune Destruction of β–Cells?, *Diabetes* 41:897–903.

Martindale, The Extra Pharmacopoeia, 28th ed., J.E.F. Reynolds, Ed., published by The Pharmaceutical Press (London), pp. 466, 467 and 473–477, 1982.

O'Connor et al., Biochim. Biophys. Acta., 1097(3), pp. 227–231 (Biosis Abs. No. 93030356), 1991.

Radomski et al., Proc. Natl. Sci USA, 87(24), pp. 10043–10047 (Biosis Abs. No. 91047745), 1990.

*Primary Examiner*—Raymond Henley, III
*Attorney, Agent, or Firm*—Howell & Haferkamp, L.C.

[57] ABSTRACT

A method is disclosed for inhibiting nitric oxide formation in a warm blooded mammal afflicted with inflammatory bowel disease which comprises administering to said mammal an effective nitric oxide inhibitory amount of aminoguanidine.

9 Claims, 8 Drawing Sheets

INHIBITION OF NITRIC OXIDE FORMATION IN INFLAMMATORY BOWEL DISEASE

CROSS-REFERENCE TO RELATED APPLICATIONS

This is a continuation-in-part of application Ser. No. 08/328,925, filed Oct. 25, 1994, now abandoned, which is in turn a continuation-in-part of application Ser. No. 08/110,915, filed Aug. 24, 1993, now U.S. Pat. No. 5,358,969, which is in turn, a continuation-in-part of application Ser. No. 07/843,387, filed Feb. 28, 1992 now U.S. Pat. No. 5,246,971, and application Ser. No. 07/906,632, filed Jun. 30, 1992, now U.S. Pat. No. 5,246,970, each of which are a continuation-in-part of application Ser. No. 07/807,912, filed Dec. 16, 1991, now abandoned all of which are incorporated by reference.

REFERENCE TO GOVERNMENT SUPPORT

This invention was made with government support under Grant Nos. DK06181, F32 DK08748, EY006600, HL39934, and DK20579 awarded by the National Institutes of Health. The government has certain rights in the invention.

BACKGROUND OF THE INVENTION

1. Field of the Invention

This invention relates to a method of inhibiting nitric oxide formation in warm blooded mammals and, more particularly, to the administration of a nitric oxide synthase inhibitor for the treatment of a pathophysiological condition manifested by acute and chronic inflammation.

2. Description of the Related Art

Nitric oxide synthase (NOS) catalyzes the mixed functional oxidation of L-arginine to L-citrulline and nitric oxide (NO•) (Stuehr et al., *Proc Natl Acad Sci USA* 88: 7773, 1991). NO• appears to function as either a signaling or an effector molecule depending on the mount produced and on the isoform of the enzyme. The constitutive isoform of nitric oxide synthase produces small mounts of NO• which activate guanylate cyclase resulting in the formation of cGMP which mediates endothelium—dependent relaxation (Moncada et al., *Pharmacol Rev* 43: 109, 1991) and neural transmission (Garthwaite, *Trends Neurol Sci* 14: 60, 1991). NO• is produced in much larger mounts by the cytokine and endotoxin inducible nitric oxide synthase (iNOS) isoform, and in macrophages functions as an effector molecule which appears to mediate the cytotoxic actions of macrophages on target cells (Hibbs et al., *Nitric Oxide from L-Arginine: A Bioregulatory System*, S. Moncada and E. Higgs, Eds. Elsevier, N.Y., pp. 189–223, 1990). Since NO• is a potent vasodilator and increases blood flow, and since vasoactive agents (such as histamine and bradykinin), which stimulate NO• production increase both blood flow and vascular permeability, NO• may be a candidate for mediating increases in blood flow and vascular permeability induced by diabetes and elevated glucose (Pugliese et al., *Diabetes/Metabolism Reviews* 7: 35, 1991).

Recently, Interleukin-1 (IL-1) has been shown to induce the expression of the cytokine inducible isoform of nitric oxide synthase in pancreatic islets. The production of NO• has been proposed to be the effector molecule which mediates IL-1's inhibitory effects on islet function (Southern et al., *FEBS Lett* 276: 42, 1990 and Corbett et al., *Biochemical J* 287: 229, 1992). Generation of an IL-1-induced EPR detectable iron-nitrosyl complex, which is prevented by $N^G$-monomethyl-L-arginine (NMMA), has been used to confirm the formation of nitric oxide by islets (Corbett et al., *J Biol Chem* 266: 21351–21354, 1991). Also, the protein synthesis inhibitor, cycloheximide has been shown to block IL-1-induced nitrite formation, cGMP accumulation, and EPR detectable iron-nitrosyl complex formation by islets, thus establishing that IL-1 induces the cytokine inducible isoform of nitric oxide synthase in pancreatic islets (Corbett et al., *Biochem J* 287: 229, 1992).

The pathogenesis of diabetic complications has been linked to imbalances in sorbitol, myo-inositol, and 1,2-diacyl-sn-glycerol metabolism, and to non-enzymatic glycation of cellular and extracellular constituents (Pugliese et al., *Diabetes/Metabolism Reviews* 7: 37, 1991). The glycation link is supported by evidence that aminoguanidine, a nucleophilic hydrazine compound, interferes with the formation of these glycation products and also attenuates the development of several diabetes-induced vascular (Pugliese et al., *Diabetes/Metabolism Reviews* 7: 35, 1991; Williamson et al., *Diabetes & Metab.* 16: 3369, 1990; Soulis-Liparota et al., *Diabetes* 40: 1328, 1991), neural (Kihara et al., *Proc Natl Acad Sci USA* 88: 6107, 1991) and collagen changes (Brownlee et al., *New Encyl J Med* 318: 1315, 1988 and Brownlee et al., *Science* 232: 1629, 1986). Bucala et al., *J Clin Invest* 87: 432 (1991) recently, reported that quenching of NO• in vitro by glycated albumin is attenuated by aminoguanidine (present during exposure of albumin to glycating agents) and suggested that glycation products may impair endothelium-dependent relaxation by attenuating NO• activity.

Inflammatory conditions are characterized by the accumulation of polymorphonuclear leukocytes, macrophages and monocytes at the site of injury. Macrophages and monocytes have been shown to produce high levels of inflammatory mediators at sites of inflammation. In the carrageenin and carrageenin-induced paw oedema models of inflammation the production of nitric oxide has also been demonstrated (Ialenti et al. *European J of Pharmacol* 211: 177–182, 1991). Macrophages are believed to be the cellular source of inducible nitric oxide synthase (iNOS) and the cell type that produces nitric oxide at the site of inflammation. Macrophage release of cytokines during the inflammatory reaction may also induce the expression of iNOS by other cellular sources. Proinflammatory prostaglandin (PGs) and thromboxane production have been demonstrated in these animal models of inflammation, the cellular source being macrophages, monocytes and fibroblasts (Masferrer et al., *Proc Natl Acad Sci USA* 91: 3228–3232, 1994). Cyclooxygenase (COX) catalyzes the first enzymatic reaction in the production of prostaglandins, prostacyclin, and thromboxane. Two isoforms of COX have been demonstrated. Constitutive COX (COX-1) is found in most tissues and is responsible for the physiological production of prostaglandins (Dewitt, *Biochim Biophys Acta* 1083: 121–143, 1991). Prostaglandins, produced by COX-1, play a prominent role in the normal physiological function of the stomach and kidney (Dewitt, supra). Expression of the other isoform of COX is inducible by cytokines. This isoform, inducible COX (COX-2), is believed to be responsible for the production of PGs under conditions of inflammation and injury (Fletcher et al., *J Biol Chem* 267: 4338–4344, 1992). Recent studies have shown the expression of COX-2 at the level of mRNA, protein, and enzymatic activity in the rat air pouch model of inflammation (Masferrer et al., supra). During this inflammation the production of PGs appears to be entirely the result of COX-2 activity (Masferrer et al., supra).

Autoimmune diabetes is an inflammatory disease that is characterized by macrophage and lymphocyte invasion of islets, followed by β-cell death (Bach, *Endocrine Rev* 15: 516–542, 1994). Cytokines released during this lymphocytic infiltration have been proposed to participate in β-cell destruction during the development of autoimmune diabetes (Corbett et al., *Diabetes* 41: 897–903, 1992). Treatment of rat islets with the cytokine IL-1, induces a potent inhibition of insulin secretion that is followed by β-cell destruction. Nitric oxide appears to mediate the inhibitory and destructive effects of IL-1 on islets. Inhibitors of nitric oxide synthase completely prevent IL-1 induced inhibition of insulin secretion and islet destruction (Corbett et al., *Autoimmunity* 15: 145–153, 1993; Corbett et al., *Diabetes* 41: 552–556, 1991). IL-1 also induces the expression of COX-2 and the production of $PGE_2$ by islets (Corbett et al., *Biochemistry* 32: 13767–13770, 1993). $PGE_2$ production by islets is attenuated by the nitric oxide synthase inhibitors NMMA, and aminoguanidine (AG) (Corbett et al., supra). These findings suggest that cytokines, nitric oxide, and nitric oxide stimulated PGs production play key roles in the development of autoimmune diabetes, in a manner similar to inflammatory conditions where the production of nitric oxide, the release of cytokines, and PGs release have been demonstrated.

Inflammatory bowel disease is another inflammatory disease and this disease is manifested as acute and chronic, non-specific intestinal inflammation of currently unknown cause. (For reviews see *Inflammatory Bowel Disease*, Dombal et al., Eds, Oxford University Press, New York, 1993; *Inflammatory Bowel Disease*, Vol. 1, Freeman, Ed, CRC Press Inc., Boca Raton, Fla., 1989; *Inflammatory Bowel Disease*, Allan et al., Eds, Churchill Livingstone, N.Y., 1990.) Conventionally, the term inflammatory bowel disease includes both ulcerative colitis and Crohn's disease. Ulcerative colitis is characterized by diffuse inflammation of the wall of the large bowel and recurrent attacks of bloody diarrhoea whereas Crohn's disease is characterized by chronic, focal inflammation of any part of the alimentary canal from the mouth to the anus. A number of non-specific mediators of inflammation have been implicated as playing a role in the initiation and maintenance of intestinal inflammation in inflammatory bowel disease although none have been identified to be the primary etiology. Immune responses, in particular, mucosal immune responses, are involved in the inflammation, however, it is not clear whether the immunologic aspects of this disease are primary or secondary events. Pathophysiologic findings at inflammatory sites include edema, infiltration of polymorphonuclear cells and the presence of lymphocytes over the chronic term of the disease. Although the etiology of inflammatory bowel disease is currently unknown, because acute and chronic inflammatory events are seen, it is possible that NO• could mediate such disease manifestations and that NOS inhibitors could have an ameliorative effect.

BRIEF DESCRIPTION OF THE INVENTION

In accordance with the present invention a novel method is provided for inhibiting nitric oxide formation in warm blooded mammals afflicted with pathophysiologic conditions manifested by acute and chronic inflammation. The method comprises administering a small but nitric oxide inhibitory effective amount of a NOS inhibitor, in particular, methyl-, dimethyl-, or amino-substituted guanidines. These inhibitory compounds are also chemically named as aminoguanidine, N,N'-diaminoguanidine, methylguanidine and 1, 1-dimethylguanidine. Other NOS inhibitory compounds are well known in the art (see, for example, Southan et al., *Biochem Pharmacol* 51: 383–394, 1996 which is incorporated by reference).

Inflammation can be conveniently divided into acute and chronic conditions. Acute inflammation is generally of relatively short duration and typically from several minutes to a few days. Its main characteristics are increased blood flow, exudation of fluid and plasma proteins (edema) and emigration of leukocytes, predominantly neutrophils. Chronic inflammation is of longer duration and is associated histologically with the presence of lymphocytes and macrophages and with proliferation of blood vessels and connective tissue. Inflammation is manifested by heat, redness, swelling, pain and loss of function. See, e.g., Cotran, Kumar and Robbins, Robbins *Pathologic Basis of Disease*, 4th ed., W. B. Saunders Company, pp. 40–41 (1989); Chandrasoma and Taylor, *Concise Pathology, First Edition*, pp. 35–44, Appleton & Lange (1991).

The causes of inflammation are numerous and include such factors as microbial infections (e.g., bacterial and fungal infections), physical agents such as burns, radiation and trauma, chemical agents such as toxins and caustic substances, necrotic tissue and various types of immunologic reactions.

The present invention is directed to the prevention/treatment of a broad spectrum of diseases which may be linked to the production of nitric oxide by leukocytes (neutrophils and macrophages) and other cells of nonhemopoietic origin as well as diseases mediated by immunologic reactions.

The treatment of acute and chronic inflammation is particularly illustrated herein in greater detail in standard state-of-the-art animal models including endotoxin-induced acute uveitis and generalized vascular leakage (Cousins et al., *Exo Eve Res* 39: 665–676, 1984 and Herbort et al., *Graefe's Arch Clin Exo Ophthalmol* 226: 553–558, 1988); IL-1-induced prostaglandin production in rat islets in vitro (Corbett et al. *Biochemistry* 32: 13767–13770, 1993); and dextran-induced inflammatory bowel disease in rats (Hirono et al., *J Natl Cancer Inst* 66: 579–583, 1981). It will be understood, however, that the method of the invention is not limited to the treatment of uveitis or autoimmune diabetes or inflammatory bowel disease, but includes treatment of other acute and chronic inflammatory diseases as mentioned above. These diseases include but are not limited to diseases such as, for example, acute and chronic infections (bacterial and fungal, including diphtheria and pertussis); acute and chronic bronchitis, sinusitis, and upper respiratory infections, including the common cold; acute and chronic gastroenteritis and colitis; acute and chronic cystitis) and urethritis; acute and chronic dermatitis; acute and chronic conjunctivitis; acute and chronic serositis (pericarditis, peritonitis, synovitis, pleuritis and tendinitis); uremic pericarditis; acute and chronic cholecystitis; acute and chronic vaginitis; drug reactions; insect bites; burns (thermal, chemical, and electrical); and sunburn.

The present invention is likewise applicable to the treatment of a variety of inflammatory disease states including infectious diseases where active infection exists at any body site, such as in the instance of meningitis. Also included are conditions such as secondary infections that may occur at a site of antigen deposition that is secondary to a primary infection at a distant body site. Specific inflammatory conditions would also include cystitis; meningitis; encephalitis; arthritis; gastroenteritis and colitis; and skin conditions such as psoriasis, whether acute or chronic; eczema; contact dermatitis; poison ivy; poison oak; poison sumac; and like inflammation-mediated conditions. Also included is the inflammation that results from alterations in leukocyte movement during infection such as sepsis and adult respiratory distress syndrome associated with sepsis.

Other inflammatory disease states include those deriving from immune disorders including involvement with T-cell and/or macrophage attachment/recognition, such as acute and delayed hypersensitivity, graft vs. host disease; primary auto-immune conditions such as pernicious anemia, and auto-immune conditions such as Type I diabetes mellitus, and rheumatoid arthritis, diseases that involve leukocyte diapedesis, such as multiple sclerosis; antigen-antibody complex mediated diseases including certain of the secondary infection states listed above; transplant rejection; stroke; myocarditis and myocardial infarcts. Inflammation due to toxic shock or trauma such as adult respiratory distress syndrome and reperfusion injury; is likewise included within the scope hereof.

DETAILED DESCRIPTION OF THE INVENTION

Figure 1:
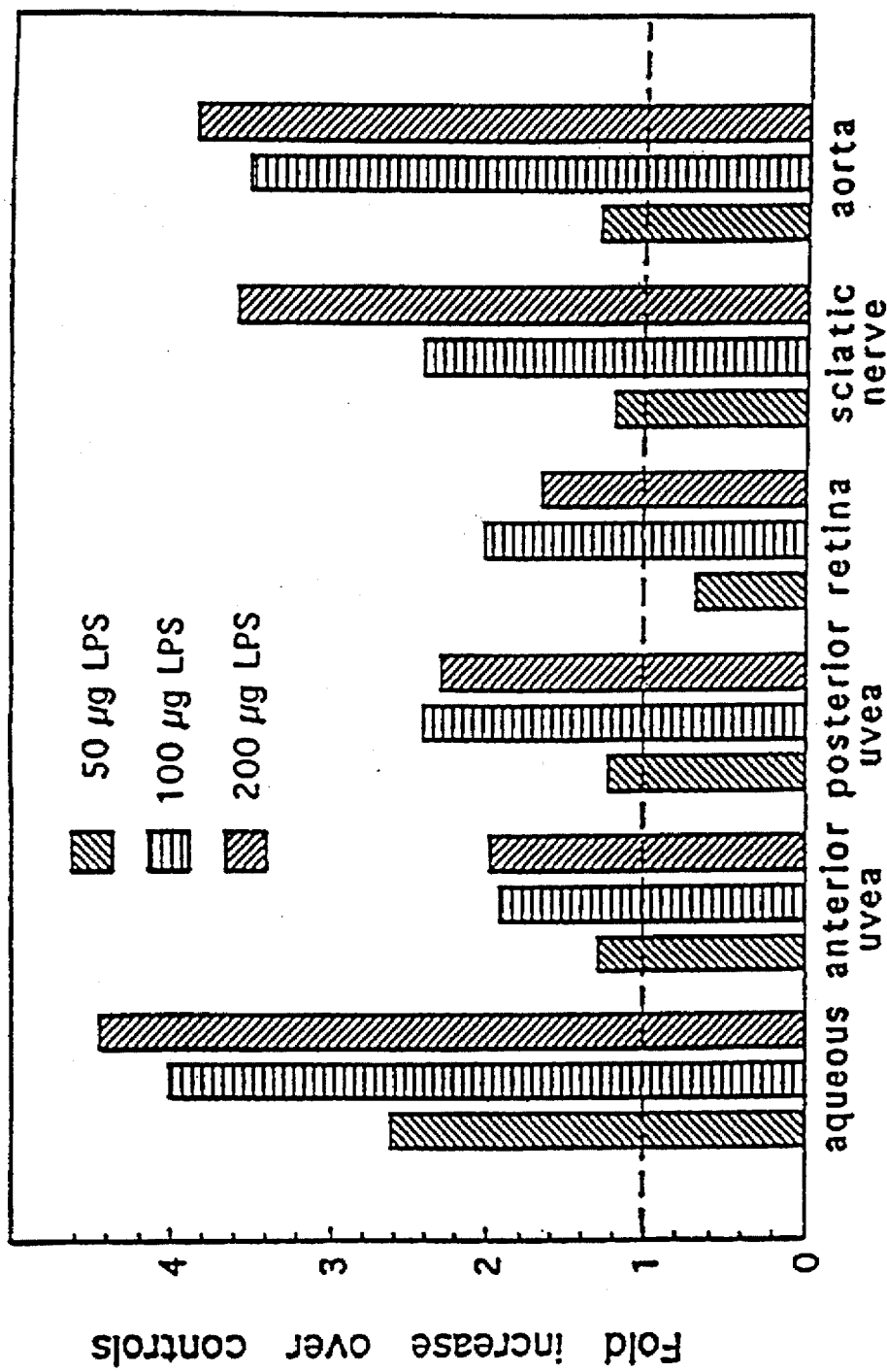
FIG. 1 is a bar graph illustrating the effect of increasing doses of lipopolysaccharide (LPS; endotoxin purified from *Salmonella minnesota*) on regional $^{125}$I-albumin permeation normalized to controls showing the fold increase (from 0 to in excess of 4-fold increase) over controls on the y axis for various tissues indicated on the x axis at three levels of LPS (50 µg, 100 µg and 200 µg LPS) as a divided dose injected into both hind footpads of Lewis rats.

While the specification concludes with claims particularly pointing out and distinctly claiming the subject matter regarded as forming the present invention, it is believed that the invention will be better understood from the following detailed description of preferred embodiments of the invention taken in conjunction with the accompanying drawings. Accordingly, the following detailed Examples further illustrate the invention although it should be understood that the invention is not limited to these specific Examples or the details described therein which are for illustrative and not limitative purposes. The results obtained in these Examples are further shown in Tables 1 to 5 hereinbelow and the accompanying FIGS. 1 to 7.

EXAMPLE 1

This example illustrates the inhibition of endotoxin-induced acute uveitis and generalized vascular leakage by aminoguanidine.

METHODS

Animals and materials

Male Lewis rats (~200 g) were purchased from Harlan Sprague Dawley (Indianapolis, Ind.) and housed and cared for in accordance with the guidelines of the Washington University Committee for the Humane Care of Laboratory Animals and in accordance with NIH guidelines on laboratory animal welfare. Rats were housed individually, fed standard rat chow (Ralston Purina, Richmond, Ind.) and water ad libitum, and were on a 12 hour light/dark cycle. Aminoguanidine (hemisulfate), and lipopolysaccharide (LPS; *Salmonella minnesota*) were purchased from Sigma (St. Louis, Mo.). $^{125}$I and $^{46}$Sc microspheres were obtained from NEN Research Products (Boston, Mass.). 1311 was obtained from ICN Biomedicals, Inc. (Costa Mesa, Calif.).

Induction of LPS-induced vascular injury

LPS was dissolved in sterile pyrogen-free 0.9% saline at concentrations of 1 µg/µl, and unless stated otherwise, 50 µl was injected into each hind footpad (100 µg total dose per rat) using metafane anesthesia as described previously by other investigators (Herbort et al., *Graefe's Arch Clin Exn Opththalmol* 226: 553–558, 1988; and Hoekzema et al., *Invest Ophthalmol Vis Sci* 33: 532–539, 1992). Control rats received an equal volume of 0.9% saline. 100 mg/kg body weight aminoguanidine was injected subcutaneously in 30 LPS-treated and in control rats at 0, 3, 6, 12, 18 and within 60 minutes of the initiation of the test, which corresponds to 20–24 hours after LPS injection.

Assessment of vascular function

Regional vascular albumin permeation was quantified by use of an isotope dilution technique based on the injection of bovine serum albumin (BSA) labeled with 2 different iodine isotopes, $^{125}$I and $^{131}$I ((Pugliese et al., *Metabolism* 39: 690–697, 1990; Pugliese et al., *Diabetes* 39: 323–332, 1990; and Pugliese et al., *Diabetes* 39: 312–322, 1990). $^{125}$I-BSA was used to quantify vascular albumin filtration after 10 min. of tracer circulation while $^{131}$I-BSA served as a plasma volume marker for correction of $^{125}$I-BSA tissue activity for tracer contained within vessels. Purified monomer IBSA (1 mg) was iodinated with 1 mCi of $^{131}$I or $^{125}$I by the iodogen, method as previously described (Pugliese et al., *Diabetes* 39: 323–332, 1990).

Rats were anesthetized with Inactin (Byk Gulden, Konstanz, FRG) (~100 mg/kg body weight injected i.p.), and core body temperature maintained at 37°±0.5° C. using heat lamps, a 37° C. surgical tray, and, a rectal temperature probe. The left femoral vein, left iliac artery, and right subclavian artery were cannulated with polyethylene tubing (0.58 mm i.d.) filled with heparinized saline (400 V heparin/ml). The femoral vein cannula was used for tracer injection and the subclavian artery cannula was connected to a pressure transducer for blood pressure monitoring. The left iliac artery was connected to a 1 ml syringe attached to a Harvard Model 940 constant withdrawal pump preset to withdraw at a constant rate of, 0.055 ml/min. The trachea was intubated and connected to a small rodent respirator for continuous ventilatory support. Microspheres were injected into the left ventricle through a carotid-artery cannula.

At time 0, $^{125}$I-albumin was injected and the withdrawal pump was started simultaneously. Eight min. after time 0, $^{131}$I-BSA was injected, followed by the microspheres. At the 10 min mark, the heart was excised to stop all blood flow, the withdrawal pump was stopped simultaneously, and various tissues were sampled for gamma spectrometry.

The left eye was dissected as previously—described (Pugliese et al., *Diabetes* 39: 323-332, 1990; and Pugliese et al., *Diabetes* 39: 312-322, 1990) and all tissue samples and arterial plasma samples were weighed, then counted in a gamma spectrometer. A quantitative index of $^{125}$I-BSA tissue clearance was calculated as previously described in (Pugliese et al., *Metabolism* 39: 690-697, 1990; Pugliese et al., *Diabetes* 39: 323-332, 1990; Pugliese et al., and *Diabetes* 39: 312-322, 1990) and expressed as µg plasma/g tissue wet weight/min. Briefly, $^{125}$I-BSA tissue activity was corrected for tracer contained within the tissue vasculature by multiplying $^{125}$I-BSA activity in the tissue by the ratio of $^{125}$I-BSA/$^{131}$I-BSA activities in the arterial plasma sample obtained at the end of the test. The vascular-corrected $^{125}$I-BSA tissue activity was divided by the time-averaged $^{125}$I-BSA plasma activity (obtained from a well mixed sample of plasma taken from the withdrawal syringe) and by the tracer circulation time (10 min) and then normalized per g tissue wet weight. To calculate blood flow, total activity of $^{46}$Sc in each ocular tissue was divided by the activity of $^{46}$Sc in the reference blood sample obtained from the withdrawal pump syringe, multiplied by the pump withdrawal rate, and expressed as ml/g tissue/min (Pugliese et al. *Diabetes* 39: 323-332 (1990) and Pugliese et al., *Diabetes* 39: 312-322 (1990)). Other non-ocular tissues (aorta, kidney, skin, skeletal muscle, sciatic nerve) also were sampled to assess if LPS induced a generalized vascular dysfunction.

Assessment of cells in aqueous humor

Aqueous fluid was collected from the left eye only (the right carotid artery was ligated for the blood flow studies and this eye was not used for function studies) using a 100 µl heparinized capillary tube and placed in a microfuge tube. Well mixed aliquots (2 µl) were spread on a siliconized glass slide, air dried, stained with Wright's stain, and the total number of cells and a differential cell count were performed using a Leitz orthoplan light microscope.

Plasma nitrate/nitrite measurements

Anticoagulated (heparin) plasma samples were centrifuged at 7500 rpm for 1 hour at 4° C. using a 10,000 molecular weight cut off Centricon filter (Areicon, Beverly, Mass.). Plasma nitrate was enzymatically reduced to nitrite using *Aspergillus niger* nitrate reductase (Sigma, St. Louis, NO). Briefly, the sample was incubated with 40 µM NADPH and 14 mU of enzyme in a final volume of 50 µl of 20 mM Tris, pH 7.6; the reaction was terminated after 5 minutes at 20° C. by dilution with 50 µl of water followed by addition of 10 µl of freshly prepared DAN reagent (0.0:5 mg/ml in 0.6M HCl) for determination of nitrite. The DAN assay is a modification of the conventional method of Damiani and Burini for the fluorometric determination of nitrite (Talanta 33, 649-652 (1986)). 2,3-Diaminonaphthalene (DAN) is reacted with nitrite under acidic conditions to form 1-(H)-naphthotriazole, a fluorescent product. After a 10 minute incubation at 20° C., the reaction was terminated with 5 µl of 2.8N NaOH, which maximizes the intensity of the fluorescent signal. Formation of the 2,3-diaminonaphthotriazole was measured using a Pandex (IDEXX Laboratories, Inc., Westbrook, Me.) fluorescent plate reader with excitation at 365 nm and emission read at 450 nm with a gain setting at 100%. Plasma nitrite levels were calculated by first subtracting the value of the enzyme blank (nitrate reductase plus NADPH) from the experimental reading, then calculating the value using a standard curve for nitrite to which NADPH was added.

Statistical analysis

All results are expressed as means±standard deviations. Overall differences among test groups for each parameter were first assessed by the Van der Waerden test, and individual pair-wise group comparisons were evaluated by at least square means analysis only if the Van der Waerden test was significant at p<0.05 for a given parameter. A nonparametric Blom transformation of all data was performed prior to assessment of individual pair-wise group differences.

RESULTS

Generalized vascular leakage of $^{125}$I-albumin

In preliminary tests, 50, 100, and 200 µg LPS were injected either as a single injection into one hind footpad or as a divided dose injected into both hind footpads of Lewis rats. In general, increases in $^{125}$I albumin leakage were greater for the divided dose of LPS versus a single injection. FIG. 1 shows changes in $^{125}$I-albumin leakage expressed as a fold increase over control values for LPS given as a divided dose. Except for sciatic nerve, maximal increases in $^{125}$I-albumin leakage normalized to control values were observed with 100 µg LPS and this dose was selected for subsequent tests.

Table 1 shows changes in $^{125}$I-albumin permeation resulting from the injection of 100 µg LPS (50 µg/footpad) into footpads of Lewis rats. The Van der Waerden test indicated highly significant group differences for $^{125}$I-albumin leakage in the retina, anterior urea, choroid/sclera, and aqueous fluid (p<0.0001), while changes were absent in brain. At the dose and frequency used, aminognanidine attenuated the $^{125}$LPS-induced $^{125}$I-albumin leakage by –75% in the retina, sciatic nerve, and aorta, by –50% in the aqueous fluid and anterior urea, and by –30% in the posterior urea, without affecting $^{125}$I-albumin leakage in controls.

Figure 2:
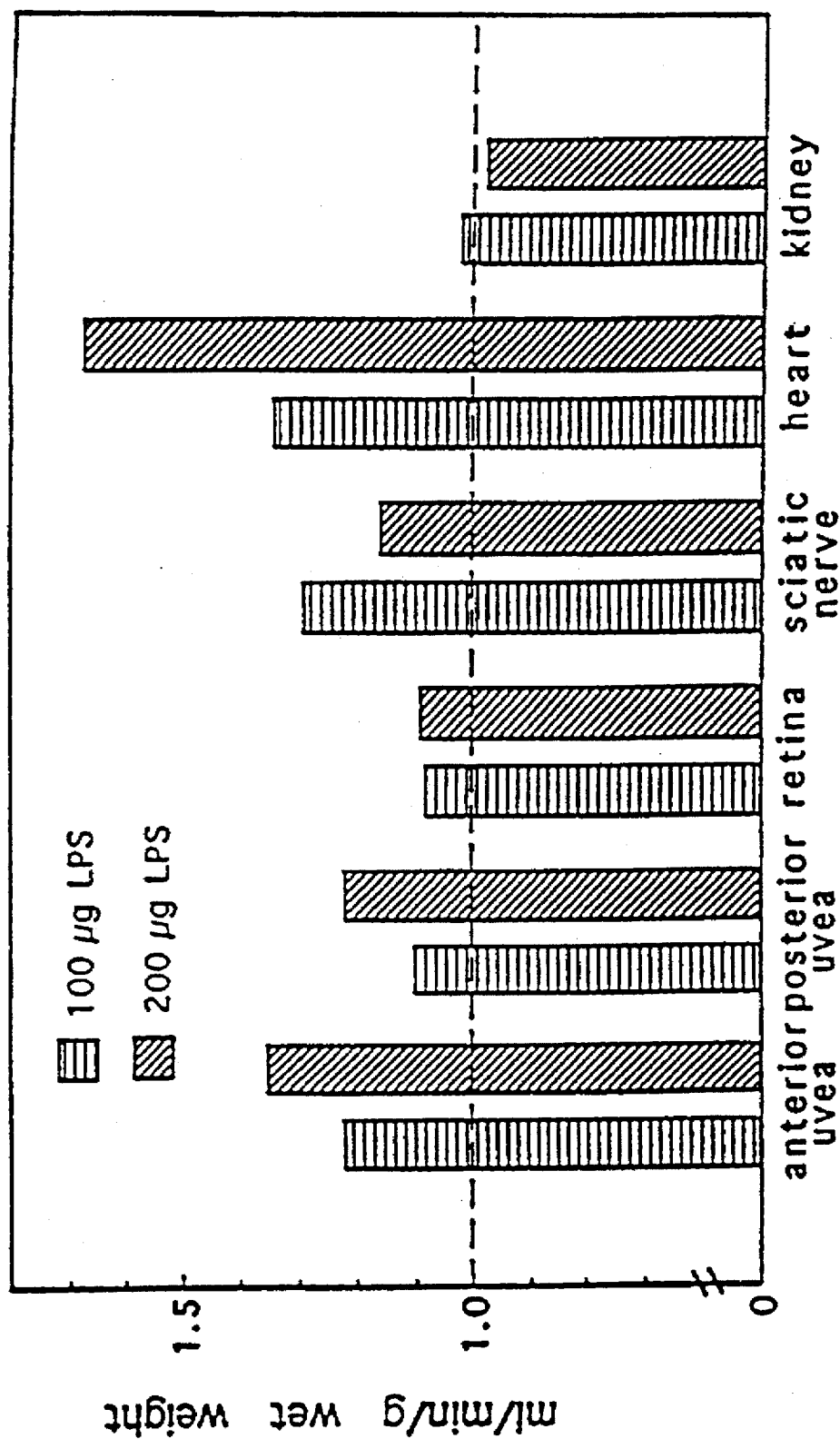
FIG. 2 is a bar graph which shows the effect of endotoxin dose on regional blood flow changes in ml/min/g wet weight shown as a fold increase (from 0 to in excess of 1.5-fold increase) on the y axis for various tissues indicated on the x axis at two levels of LPS (100 µg and 200 µg) as a divided dose injected into Lewis rats.

FIG. 2 shows changes in regional blood flows expressed as a fold increase over control values for LPS administered as a divided dose. Regional blood flows increased with increasing dose of LPS in the anterior and posterior uveal vasculatures and in the heart, plateaued in the-retinal and sciatic nerve at 100 µg LPS, and was unaffected by LPS in the kidney when measured 20 hours after LPS injection. The Van der Waerden test indicated significant group differences for blood flow in the anterior uvea and choroid/sclera but not in the retina, sciatic nerve, brain, heart, and kidney (Table 2). LPS increased blood flow ~40% in the anterior uvea and ~25% in the choroid-sclera and these increases were prevented by aminoguanidine.

Gravimetric and hemodynamic parameters

All gravimetric and hemodynamic parameters, including body weight, mean arterial blood pressure, cardiac output, cardiac index, total peripheral resistance, GFR (normalized either to whole kidney or g kidney wet weight), glomerular filtration fraction, and renal vascular resistance, were unaffected by the injection of 100 µg LPS (Table 3).

Aqueous fluid leukocyte cell counts

Figures 3A, 3B:
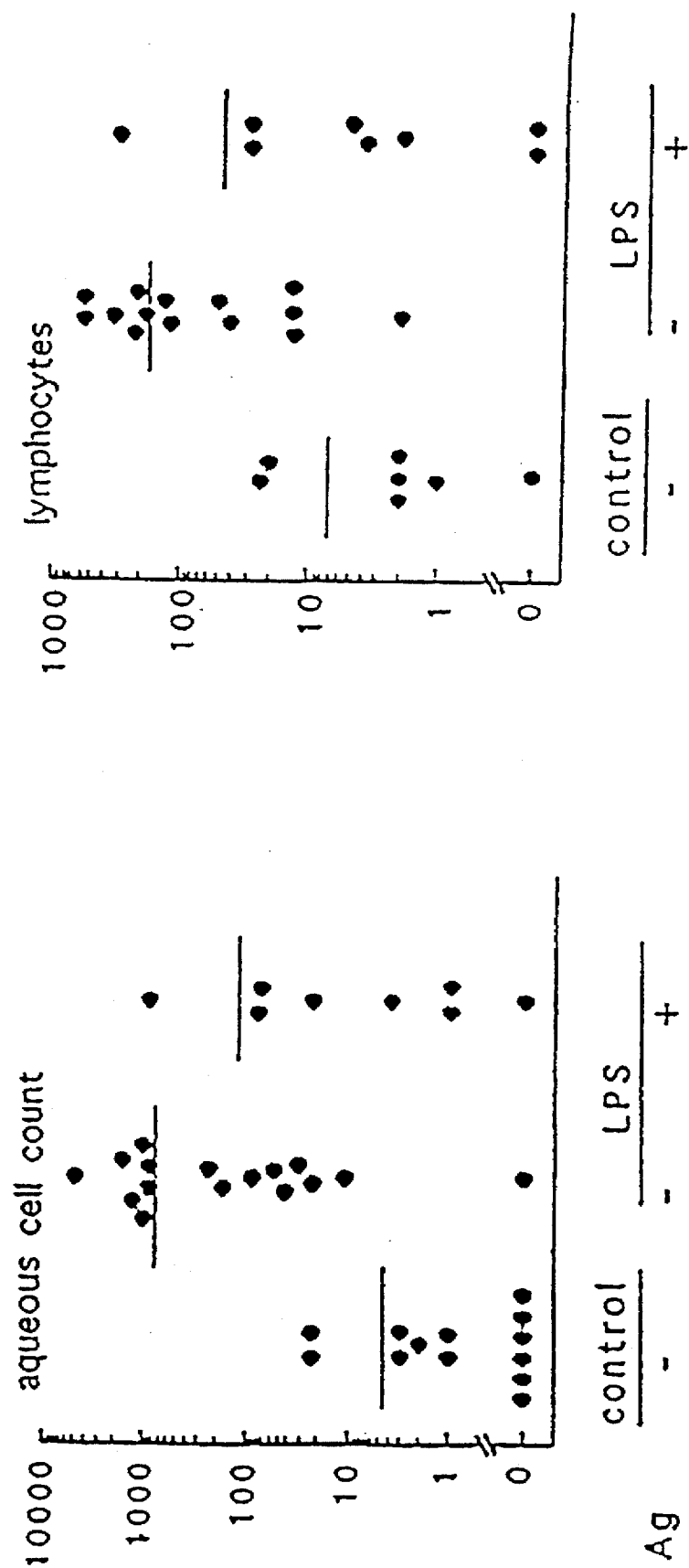
FIG. 3 graphically represents aqueous fluid leukocyte cell counts in Lewis rats treated with 100 µg LPS, showing (A) cell counts of the aqueous fluid and cell counts for three types of infiltrating cells into the aqueous fluid, (B) lymphocytes, (C) monocytes and (D) PMN's expressed on the y axis in a logarithmic scale and on the x axis the groups of controls (−) and LPS-treated animals before (−) and after (+) treatment with aminoguanidine (Ag) (100 mg/kg) on the x axis, each filled in circle (●) representing the cell count from an individual rat.
Figures 3C, 3D:
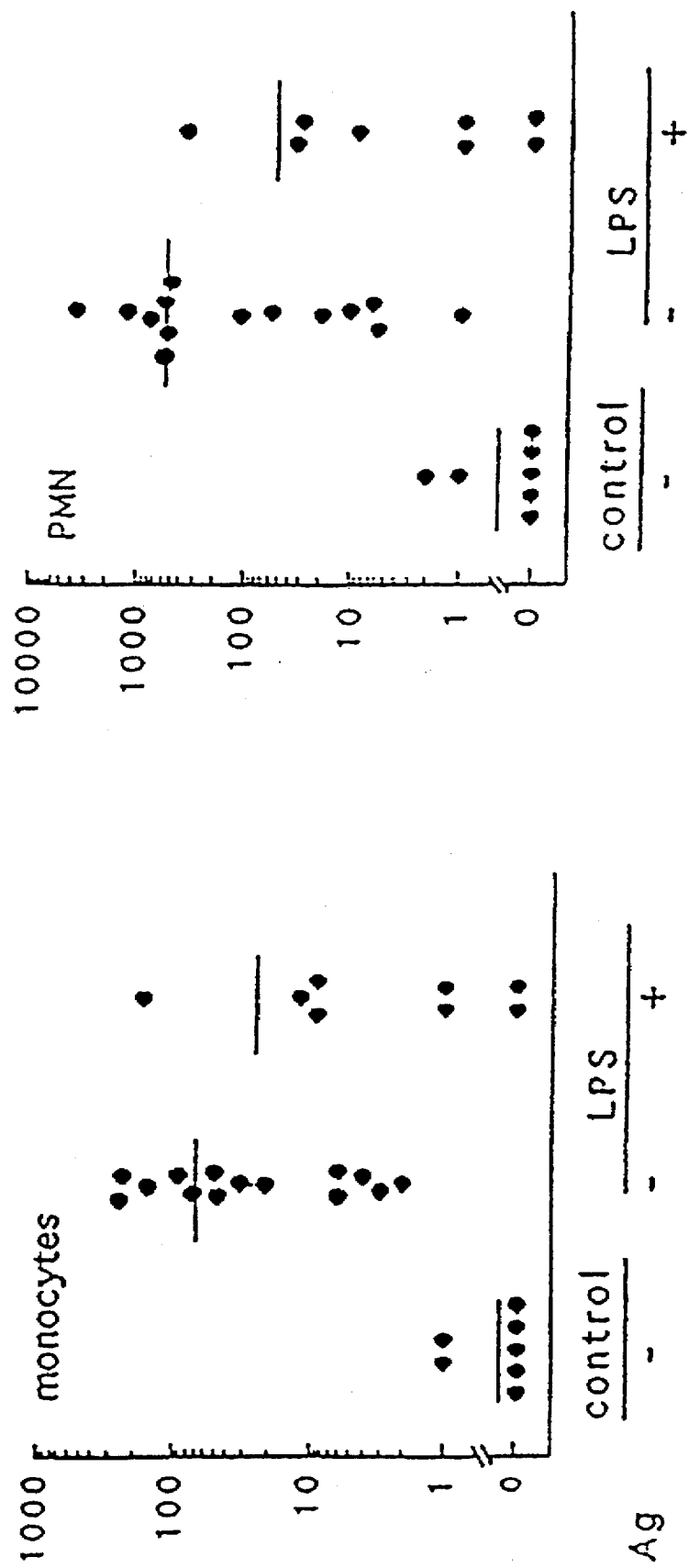

Number of cells in a well mixed 2 µl sample of aqueous fluid from controls was low, ranging from no cells in 6 animals to ~25 cells in 2 rats (FIG. 3); the median value was ~5 cells/2 µl fluid and was unaffected by aminoguanidine treatment in controls. As shown in FIG. 3A, 100 µl LPS significantly increased the number of cells in 2 µl of aqueous fluid. FIG. 3 also shows the types of infiltrating cells into the aqueous fluid following LPS injection. Virtually all cells in the aqueous fluid of controls (±aminoguanidine) were lymphocytes. In aqueous fluid of rats treated with 100 µg LPS, lymphocytes (FIG. 3B), monocytes (FIG. 3C), and PMNs (FIG. 3D) increased significantly with the largest increase observed for PMNs. Aminoguanidine reduced the total number of cells in the aqueous fluid of LPS-treated rats, including ~90% reduction in the number of PMNs.

Plasma nitrate/nitrite measurement

Figure 4:
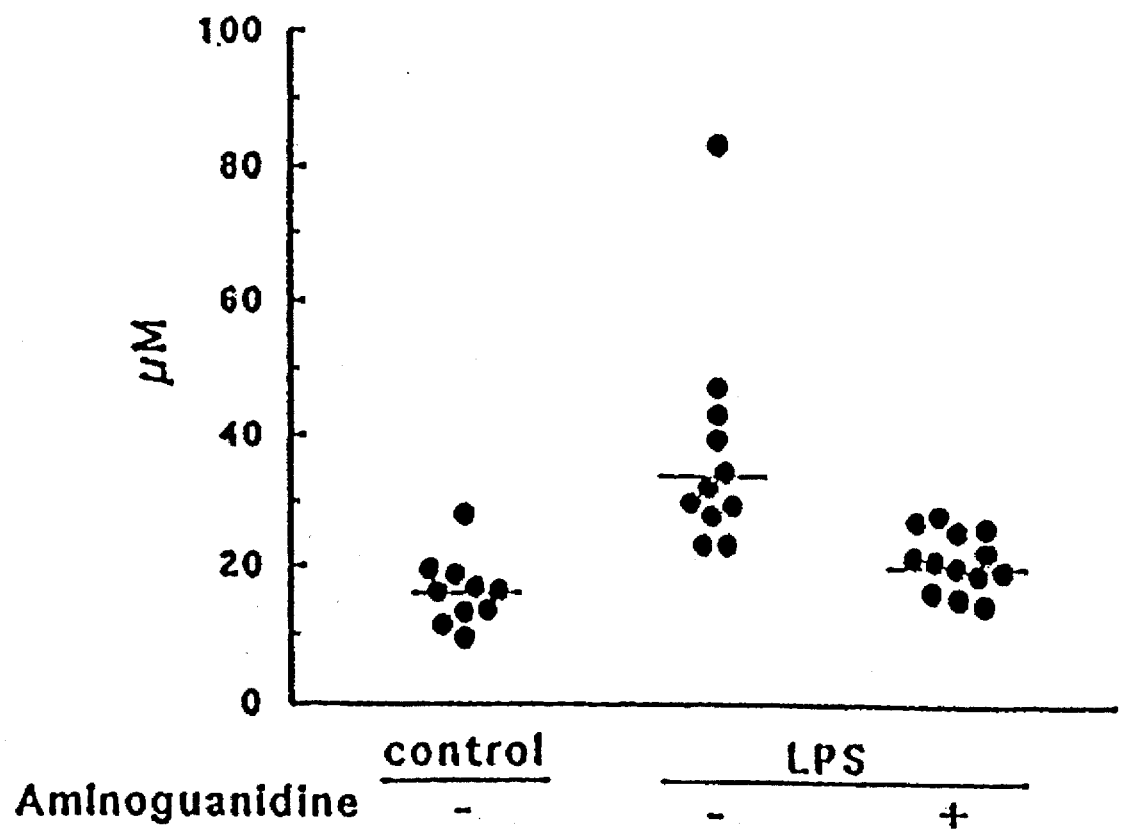
FIG. 4 graphically represents the effect of aminoguanidine on plasma nitrate/nitrite levels in Lewis rats treated with 100 µg LPS showing on the y axis the plasma nitrate/nitrite levels in lag and on the x axis the groups of control (−) and LPS-treated animals before (−) and after (+) treatment with aminoguanidine (100 mg/ks)

Plasma nitrate/nitrite levels were 17.9±8.6 µM for controls and were increased ~65% in LPS—treated rats (FIG. 4). Aminoguanidine treatment prevented the LPS—induced increases in plasma nitrate/nitrite levels.

It is seen from the above results that aminoguanidine markedly attenuated manifestations of endotoxin-induced acute uveitis (vascular-leakage, increased blood flow, and exudation of leukocytes into the aqueous fluid) as well as elevated plasma nitrate/nitrite levels. Aminoguanidine also significantly attenuated or completely prevented systemic effects of endotoxin on vascular leakage, i.e., edema (an important manifestation/consequence of inflammation) in nerve, aorta, and small intestine.

TABLE 1

Effects of LPS (100 µg) and aminoguanidine (100 mg/kg) on regional $^{125}$I-albumin permeation (µg plasma/min/g wet weight)

| | control | LPS | LPS + aminoguanidine |
|---|---|---|---|
| number of rats | 14 | 19 | 11 |
| eye | | | |
| aqueous fluid | 65 ± 23[a] | 294 ± 81[b] | 204 ± 53[b,f] |
| anterior uvea | 270 ± 53 | 611 ± 110[b] | 423 ± 67[b,e] |
| posterior uvea | 258 ± 75 | 612 ± 110[b] | 497 ± 96[b,f] |
| retina | 66 ± 14 | 154 ± 32[b] | 86 ± 23[e] |
| sciatic nerve | 62 ± 14 | 167 ± 35[b] | 91 ± 20[c,e] |
| aorta | 75 ± 26 | 245 ± 64[b] | 114 ± 43[d,e] |
| skeletal muscle | 44 ± 17 | 62 ± 11 | 51 ± 10 |
| skin | 110 ± 27 | 209 ± 73[b] | 186 ± 49[c] |
| brain | 23 ± 11 | 24 ± 11 | 25 ± 15 |
| heart | 621 ± 57 | 585 ± 116 | 624 ± 86 |
| small intestine | 377 ± 112 | 567 ± 247[d] | 375 ± 100[g] |
| kidney | 612 ± 212 | 1,173 ± 407[b] | 1,578 ± 251[b,f] |

Male Lewis rats were treated with 100 µg LPS (50 pg in each hind footpad) ± 100 mg/kg body weight aminoguanidine hemisulfate (at the time of injection of LPS and 3, 6, 12, 18, and 20–24 hours thereafter). LPS was injected at noon and the animals were sacrificed the following morning.
[a]values are mean ± SD
Significantly different from controls by least square means analysis:
[b]p<0.0001;
[c]p<0.0001;
[d]p<0.005
Significantly different from LPS-treated rats least square means analysis:
[e]p<0.0001;
[f]p<0.0005;
[g]p<0.0005

TABLE 2

Effects of LPS (100 µg) and aminoguanidine (100 mg/kg) on regional blood flows (ml/min/g wet weight)

| | control | LPS | LPS + aminoguanidine |
|---|---|---|---|
| number of rats | 11 | 13 | 9 |
| eye | | | |
| anterior uvea | 1.8 ± 0.4 | 2.5 ± 0.6[b] | 1.9 ± 0.3[d] |
| posterior uvea | 3.4 ± 0.6 | 4.3 ± 0.9[c] | 3.7 ± 0.4 |
| retina | 0.42 ± 0.03 | 0.45 ± 0.07 | 0.42 ± 0.04 |
| sciatic nerve | 0.07 ± 0.01 | 0.08 ± 0.03 | 0.08 ± 0.03 |
| brain | 0.6 ± 0.1 | 0.6 ± 0.1 | 0.6 ± 0.1 |

TABLE 2-continued

Effects of LPS (100 µg) and aminoguanidine (100 mg/kg) on regional blood flows (ml/min/g wet weight)

| | control | LPS | LPS + aminoguanidine |
|---|---|---|---|
| heart | 4.9 ± 1.4 | 6.1 ± 1.2 | 5.4 ± 1.7 |
| kidney | 4.8 ± 0.9 | 4.7 ± 0.6 | 4.9 ± 0.6 |

Male Lewis rats were treated with 100 ± LPS (50 µg in each hind footpad) ± 100 mg/kg body weight aminoguanidine hemisulfate (at the time of injection of LPS and 3, 6, 12, 18, and 20–24 hours thereafter). LPS was injected at noon and the animals were sacrificed the following morning.
[a]values are mean ± SD
Significantly different from controls by least square means analysis:
[b]p<0.0001;
[c]p<0.005
Significantly different from LPS-treated rats least square means analysis:
[d]p<0.005

TABLE 3

Effects of LPS (100 µg) and aminoguanidine (100 mg/kg) on gravimetric and hemodynamic parameters

| | control | LPS | LPS + aminoguanidine |
|---|---|---|---|
| number of rats | 5 | 6 | 7 |
| body weight (g) | 237 ± 15[a] | 225 ± 9 | 229 ± 12 |
| mean arterial blood pressure (mm Hg) | 120 ± 9 | 121 ± 9 | 124 ± 10 |
| cardiac output (ml/min) | 81 ± 9 | 75 ± 4 | 77 ± 3 |
| cardiac index (ml/min/100 g b.w.) | 343 ± 19 | 334 ± 13 | 336 ± 23 |
| total peripheral resistance (mm Hg/ml/min) | 1.42 ± 0.10 | 1.55 ± 0.14 | 1.54 ± 0.11 |
| GFR (ml/min/whole kidney) | 0.96 ± 0.07 | 0.97 ± 0.06 | 0.95 ± 0.14 |
| GFR (ml/min/g kidney) | 0.87 ± 0.07 | 0.90 ± 0.11 | 0.87 ± 0.15 |
| filtration fraction (GFR/renal blood flow) | 0.34 ± 0.08 | 0.34 ± 0.05 | 0.31 ± 0.06 |
| renal vascular resistance (mm Hg/ml/min) | 0.97 ± 0.07 | 0.97 ± 0.06 | 0.95 ± 0.14 |

Male Lewis rats were treated with 100 µg LPS (50 µg in each hind footpad) ± 100 mg/kg body weight aminoguanidine hemisulfate (at the time of injection of LPS and 3, 6, 12, 18, and 20–24 hours thereafter). LPS was injected at noon and the animals were sacrificed the following morning.
[a]values are mean ± SD

EXAMPLE 2

This example illustrates the inhibition of endotoxin-induced acute uveitis and generalized vascular leakage by methylguanidine.

METHODS

Animals and Materials

Male Lewis rats (~200 g) were purchased from Harlan Sprague Dawley (Indianapolis, Ind.) and housed and cared for in accordance with the guidelines of the University Committee for the Humane Care of Laboratory Animals in accordance with NIH guidelines on laboratory animal welfare. Rats were housed individually, fed standard rat chow (Ralston Purina, Richmond, Ind.) and water ad libitum, and were on a 12 hour light/dark cycle. Methylguanidine (hydrochloride) and lipopolysaccharide (LPS; *Salmonella minnesota*) were purchased from Sigma (St. Louis, Mo.).

$^{125}$I was obtained from NEN Research Products (Boston, Mass.). $^{131}$I was obtained from ICN Biomedicals, Inc. (Costa Mesa, Calif.).

Induction of LPS-Inducted Vascular Injury

LPS was dissolved in sterile pyrogen-free 0.9% saline at concentrations of 1 µg/µl, and 50 µl was injected into each hind footpad (100 µg total dose per rat) using metafane anesthesia as described previously by other investigators (Herbort et al., *Graefe's Arch Clin Exp Ophthalmol* 226: 553–558 (1988); and Hoekzema et al., *Invest Ophthalmol Vis Sci* 33: 532–539 (1992)). Control rats received an equal volume of 0.9% saline. 50 mg/kg body weight methylguanidine was injected subcutaneously in LPS-treated and in control rats at 0, 3, 6, 12, 18 and 20–24 hours after LPS injection. Animals were killed for the vascular function studies 20 to 24 hours after LPS injection.

Assessment of Vascular Function

Regional vascular albumin permeation was quantified by use of an isotope dilution technique based on the injection of bovine serum albumin (BSA) labeled with 2 different iodine isotopes, $^{125}$I and $^{131}$I (Pugliese et al., *Metabolism* 39: 690–697, 1990; Pugliese et al., *Diabetes* 39: 323–332, 1990; and Pugliese et al., *Diabetes* 39: 312–322, 1990). $^{125}$I-BSA was used to quantify vascular albumin filtration after 10 minutes of tracer circulation, while $^{131}$I-BSA served as a plasma volume marker for correction of $^{125}$I-BSA tissue activity for tracer contained within vessels. Purified monomer BSA (1 mg) was iodinated with 1 mCi of $^{131}$I or $^{125}$I by the iodogen method as previously described in Pugliese et al., *Diabetes* 39: 323–332, 1990.

Rats were anesthetized with Inactin (Byk Gulden Konstanze, FRG) (~100 mg/kg body weight injected i.p.), and core body temperature maintained at 37°±0.5° C. using heat lamps, a 37° C. surgical tray, and a rectal temperature probe. The left femoral vein, left iliac artery, and right subclavian artery were cannulated with polyethylene tubing (0.58 mm i.d.) filled with heparinized saline (400 U heparin/ml). The femoral vein cannula were used for tracer injection and the subclavian artery cannula was connected to a pressure transducer for blood pressure monitoring. The left iliac artery was connected to a 1 ml syringe attached to a Harvard Model 940 constant withdrawal pump preset to withdraw at a constant rate of 0.055 ml/min. The trachea was intubated and connected to a small rodent respirator for continuous ventilatory support.

At time 0, $^{125}$I-albumin was injected i.v. and the withdrawal pump was started simultaneously. Eight minutes after time 0, $^{131}$I-BSA was injected. At the 10 minute mark, the heart was excised to stop all blood flow, the withdrawal pump was stopped simultaneously, and various tissues were sampled for gamma spectrometry. The left eye was dissected as previously described (Pugliese et al., *Diabetes* 39: 323–332, 1990 and Pugliese et al., *Diabetes* 39: 312–322, 1990) and all tissue samples and arterial plasma samples were weighed, then counted in a gamma spectrometer. A quantitative index of $^{125}$I-BSA tissue clearance was calculated as previously described (Pugliese et al., *Metabolism* 39: 690–697 (1990); Pugliese et al., *Diabetes* 39: 323–332 (1990); and Pugliese et al., *Diabetes* 39: 312–322 (1990)) and expressed as µg plasma/g tissue wet weight/min. Briefly, $^{125}$I-BSA tissue activity was corrected for tracer contained within the tissue vasculature by multiplying $^{125}$I-BSA activity in the tissue by the ratio of $^{125}$I-BSA/131I-BSA activities in the arterial plasma sample obtained at the end of the test. The vascular corrected $^{125}$I-BSA tissue activity was divided by the time-averaged $^{125}$I-BSA plasma activity (obtained from a well-mixed sample of plasma taken from the withdrawal syringe) and by the tracer circulation time (10 minutes) and then normalized per g tissue wet weight. Other non-ocular tissues (aorta, kidney, skin, skeletal muscle, sciatic nerve) also were sampled to assess if LPS induced a generalized vascular dysfunction.

Statistical Analysis

All results are expressed as means±standard deviations. Overall differences among test groups for each parameter were assessed by Students' test.

Generalized Vascular Leakage of $^{125}$I-Albumin

Table 4 shows changes in $^{125}$I-albumin permeation resulting from the injection of 100 µg LPS (50 µg/footpad) into footpads of Lewis rats. Highly significant group differences for $^{125}$I-albumin leakage were evident in the aqueous fluid, anterior uvea, choroid/sclera, retina, sciatic nerve, aorta, and kidney ($p<0.0001$), while smaller increases were observed in the skin and skeletal muscle. No LPS-induced changes were present in brain, heart, or small intestine. At the dose and frequency used, methylguanidine attenuated the LPS-induced $^{125}$I-albumin leakage in aqueous fluid, anterior uvea, and kidney and prevented the LPS-induced increases in albumin leakage in the choroid/sclera, retina, sciatic nerve, aorta, and skin.

It is seen from the above results that methylguanidine (at approximately one-half of the dose of aminoguanidine used in Example 1) was as effective as (or more effective than) aminoguanidine in preventing endotoxin-induced vascular leakage (an important manifestation/consequence of inflammation) in uveal tissue as well as in the sciatic nerve, aorta, skeletal muscle, skin, and kidney.

Similar results as obtained in Examples 1 and 2 can be obtained by substituting N,N'-diaminoguanidine or 1,1-dimethylguanidine for equivalent amounts of aminoguanidine or methylguanidine, respectively, in said Examples.

TABLE 4

Effects of LPS µg) and methylguanidine (mg) on regional $^{125}$I-albumin permeation[a]

|  | control | LPS | LPS + methylguanidine |
|---|---|---|---|
| number of rats | 5 | 8 | 4 |
| aqueous | 154 ± 100 | 495 ± 283[a] | 335 ± 30[c] |
| anterior uvea | 266 ± 52 | 618 ± 106[a] | 383 ± 32[c,e] |
| choroid/sclera | 298 ± 67 | 582 ± 77[a] | 357 ± 50[d] |
| retina | 68 ± 15 | 168 ± 28[a] | 67 ± 7[d] |
| sciatic nerve | 71 ± 14 | 187 ± 32[a] | 69 ± 3[d] |
| aorta | 75 ± 24 | 211 ± 43[a] | 102 ± 8[d] |
| skeletal muscle | 54 ± 19 | 103 ± 46[c] | 63 ± 11 |
| skin | 99 ± 29 | 224 ± 65[b] | 106 ± 16[f] |
| brain | 20 ± 4 | 25 ± 6 | 19 ± 5 |
| heart | 623 ± 43 | 699 ± 58 | 629 ± 82 |
| small intestine | 414 ± 40 | 559 ± 147 | 423 ± 188 |
| kidney | 635 ± 239 | 1,561 ± 221[a] | 1,042 ± 253[c,e] |

[a]µg plasma/g wet weight/min; values are mean ± SD.
Male, Lewis rats were treated with 100 µg LPS (50 pg in each hind footpad) ± 50 mg/kg body weight methylguanidine hydrochloride (at the time of injection of LPS and 3, 6, 12, 18, and 20–24 hours thereafter). LPS was injected at noon and the animals were sacrificed the following morning.
Significantly different from untreated controls:
[a]p<00001;
[b]p<0.005;
[c]p<0.05
Significantly different from LPS:
[d]p<0.001;
[e]p<0.005;
[f]p<0.01

EXAMPLE 3

This example illustrates the effect of aminoguanidine on prostaglandin production as measured by the activity of cyclooxygenase-2 (COX-2), a primary source of prostaglandins during inflammation.

Figure 6:
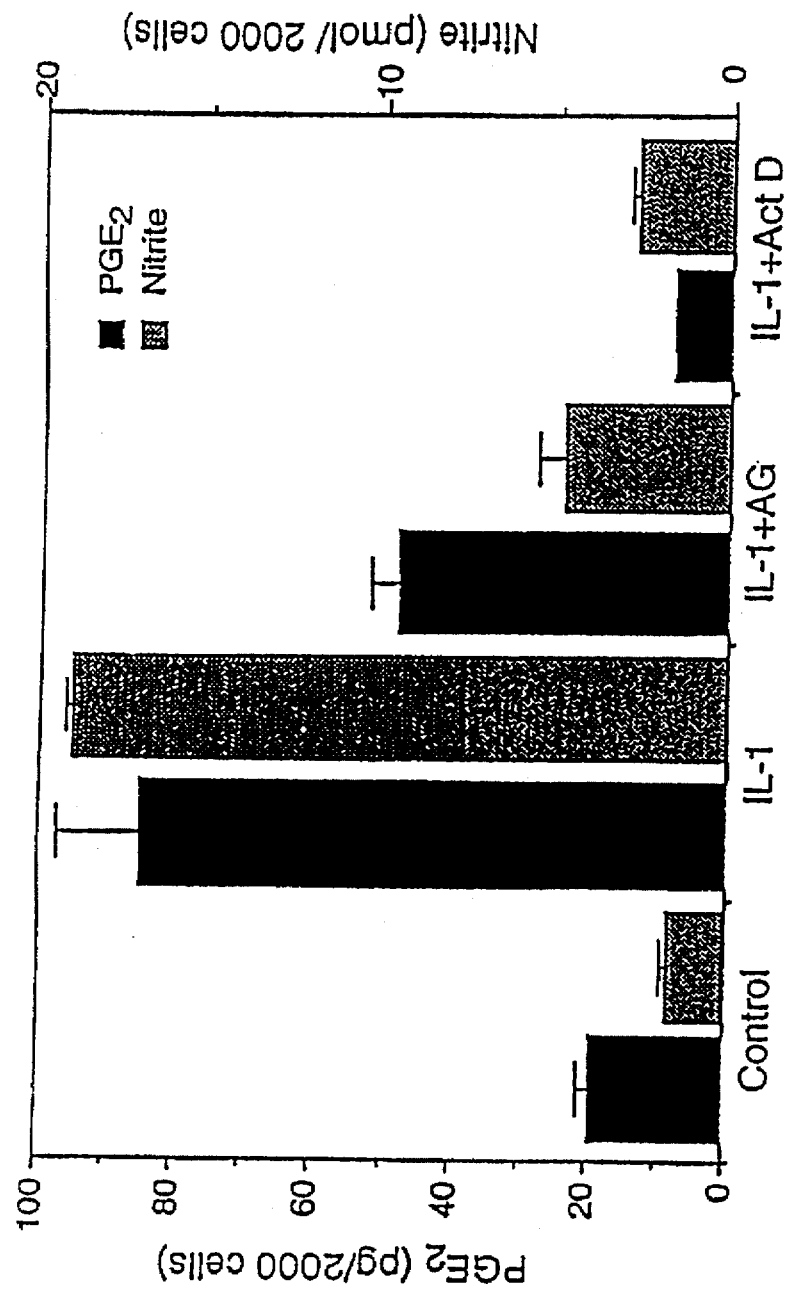
FIG. 6 is a graph demonstrating that aminoguanidine attenuates IL-1-induced $PGE_2$ production by purified β-cells.
Figure 7:
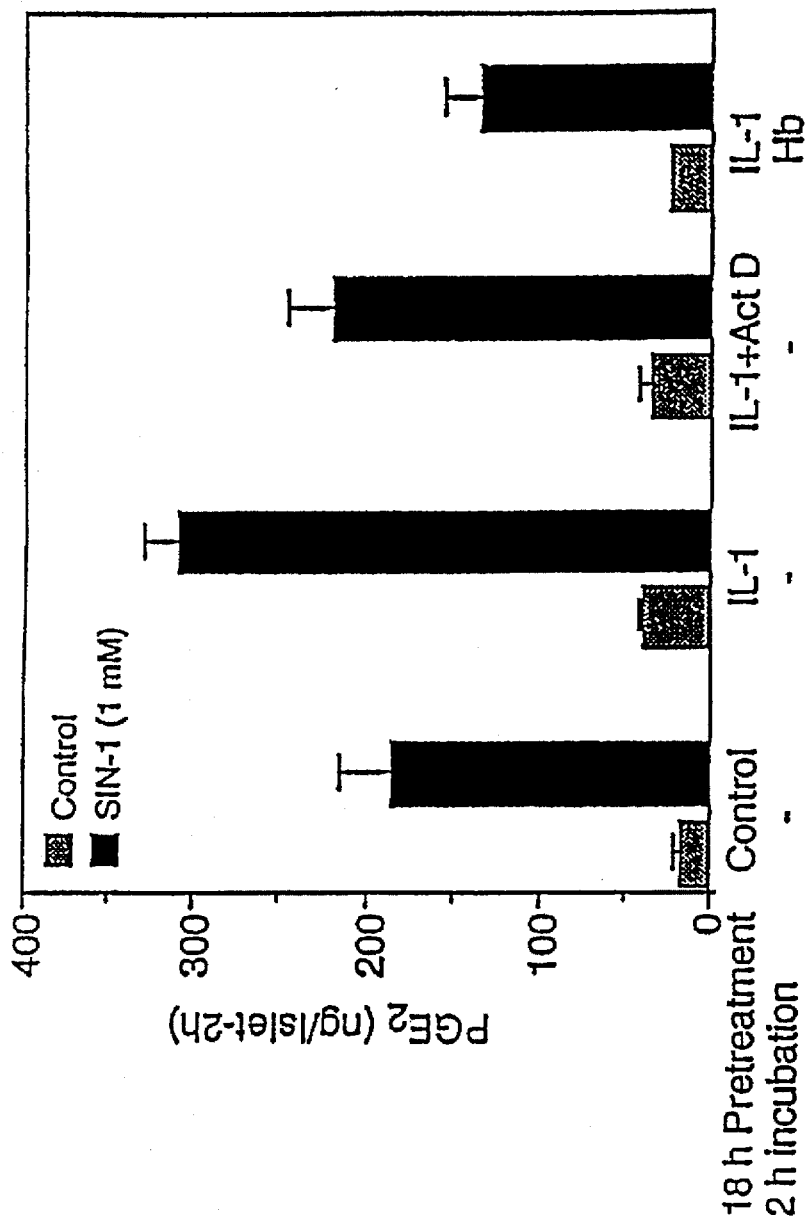
FIG. 7 is a graph demonstrating that exogenous nitric oxide stimulates $PGE_2$ production by rat islets.

The nitric oxide synthase inhibitor, NMMA has been shown by the inventors herein to attenuate IL-1β-induced nitrite and $PGE_2$ production (Corbett et al. *Biochemistry* 32: 13767–13770, 1993 which is incorporated by reference). The present data as set forth in FIGS. 5–7 demonstrate the direct activation by nitric oxide of the enzymatic activity of COX-2 resulting in the overproduction of $PGE_2$. Inhibitors of nitric oxide synthase (AG, and NMMA) attenuate nitric oxide stimulated production of $PGE_2$. These inhibitors do not have inhibitory effects on the expression of either iNOS or COX-2(9). Exogenous production of nitric oxide (spontaneously released by nitric oxide donor compound, SIN-1) stimulates the production of $PGE_2$ by islets, further supporting the direct activation of COX by nitric oxide (FIG. 7). These studies support the use of iNOS inhibitors, NMMA and AG for the inhibition of PGs production under inflammatory conditions such as acute and chronic inflammation, arthritis, inflammatory bowel disease, injury, etc. The inhibitors function by preventing nitric oxide activation of COX-2.

Figure 5:
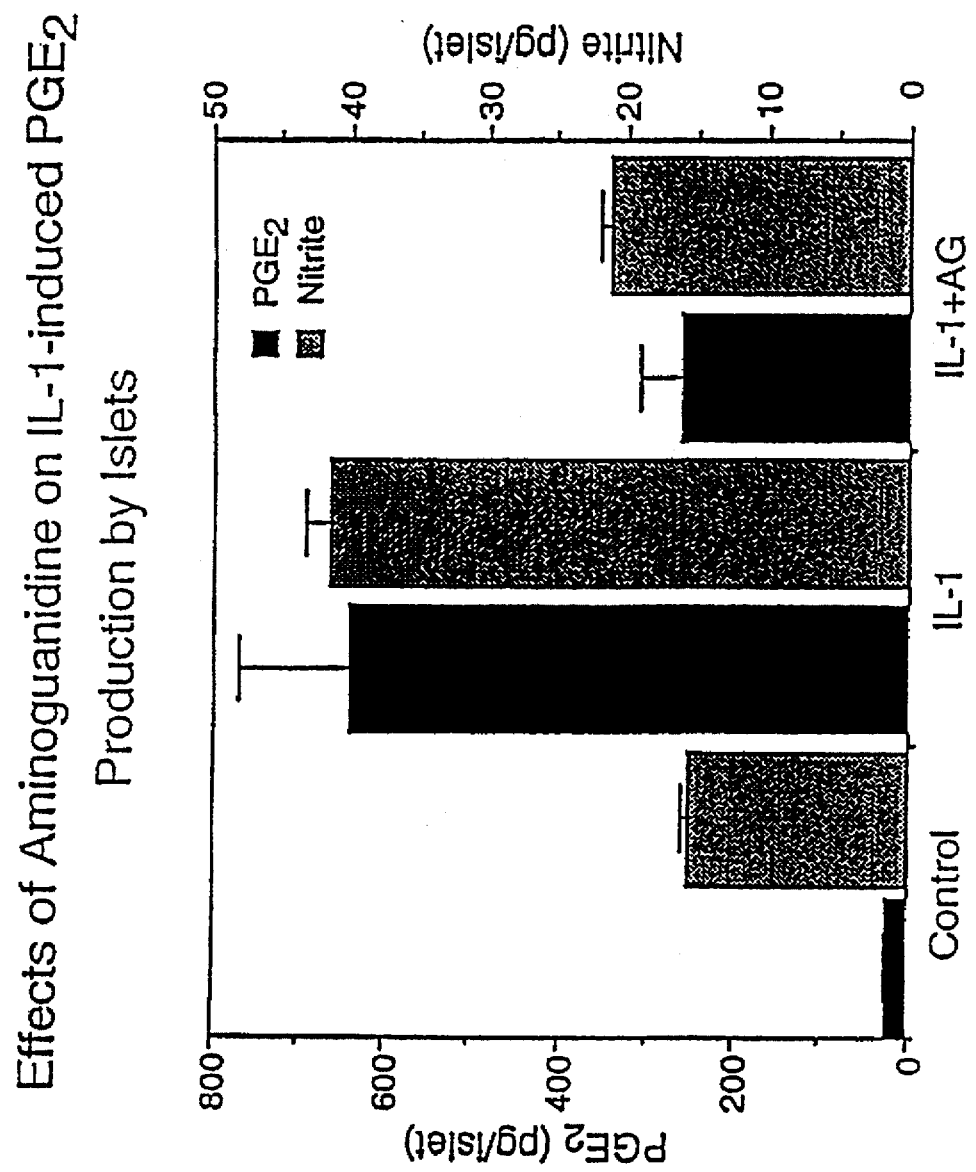
FIG. 5 is a graph demonstrating that aminoguanidine attenuates IL-1-induced $PGE_2$ production by rat islets.

The experimental procedures were as set forth in Corbett et al. *Biochemistry* 32: 13767–13770, 1993 except as indicated below. Isolated rat islets were incubated for 24 h in the absence or presence of IL-1 (5 units/ml), or IL-1 (5 units/ml)+0.5 mM aminoguanidine (AG), the supernatant was removed and both $PGE_2$ and nitrite formation were determined. The results demonstrate that aminoguanidine (AG) attenuates IL-1-induced $PGE_2$ and almost completely prevents IL-1-induced nitrite formation by rat islets (FIG. 5). These findings indicate that IL-1-induces COX-2 and iNOS expression and that nitric oxide directly activates COX-2.

In a further experiment, purified β-cells were incubated for 24 h in the absence or presence of IL-1 (5 units/ml), IL-1 (5 units/ml)+0.5 mM aminoguanidine, or IL-1 (5 units/ml) +1 μM Actinomycin D. The supernatant was removed and $PGE_2$ and nitrite formation were determined. Again in these experiments, aminoguanidine attenuated IL-1-induced $PGE_2$ production and almost completely prevented IL-1-induced nitrite formation by β-cells (FIG. 6). The transcriptional inhibitor actinomycin D also substantially diminished PGE-2 and nitrite formation by β-cells, indicated the requirement for mRNA transcription. These findings indicate that IL-1-induces COX-2 and iNOS expression and that nitric oxide directly activates COX-2.

As further corroboration of the activity and interaction of nitric oxide in COX and $PGE_2$ production, rat islets were pretreated with IL-1 (5 units/ml) or IL-1 and actinomycin D (1 μM) for 18 h. The islets were washed and then cultured for 2 h with 30 μM arachidonic acid (COX substrate) in the presence or absence of the nitric oxide donor compound, SIN-1 (1 mM) and the nitric oxide scavenger, hemoglobin (Hb) as indicated. The results are presented in FIG. 7 and demonstrate that nitric oxide, released spontaneous by SIN-1, stimulates the activity of both constitutive COX (COX-1; control and IL-1+Act D treatment) and inducible COX (COX-2; IL-1 treated group). Hemoglobin attenuates SIN-1 stimulated $PGE_2$ formation indicating that the effects of SIN-1 on COX activity is mediated by nitric oxide.

EXAMPLE 4

The following example illustrates the inhibition by aminoguanidine of the vascular injury in a rat model of inflammatory bowel disease.

Inflammatory bowel disease was induced by feeding male Sprague-Dawley rats pulverized normal rat chow containing 5% dextran sodium sulfate (DSS), mol wt ~40–50,000. This model is reported to induce loose stools/diarrhea in all animals within 14 days which is followed by extensive ulceration of the colon and eventually by development of carcinomas of the colon (65% of animals by 134 days) (Hirono et al., *J Natl Cancer Inst* 66: 579–583, 1981). Thus the model reproduces many of the characteristic features of chronic ulcerative colitis in humans, including the development of cancer.

METHODS

Animals and materials

Male Lewis rats (~200 g) were purchased from Harlan Sprague Dawley (Indianapolis, Ind.) and housed and cared for in accordance with the guidelines of the Washington University Committee for the Humane Care of Laboratory Animals and in accordance with NIH guidelines on laboratory animal welfare. Rats were housed individually, fed standard rat chow (Ralston Purina, Richmond, Ind.) and were on a 12 hour light/dark cycle. Aminoguanidine (hemisulfate) was purchased from Sigma (St. Louis, Mo.). $^{125}I$ and $^{46}Sc$ microspheres were obtained from NEN Research Products (Boston, Mass.).

Induction of Inflammatory-Bowel-Disease vascular injury

Based on pilot studies, 4 groups of rats were prepared as follows:
1. Control rats fed normal rat chow (n=9),
2. Rats fed chow containing 5% DSS (n=8),
3. Rats fed chow with 5% DSS+aminoguanidine hemisulfate added to the drinking water in a concentration to provide a daily dose of 25 mg/kg body weight/day (n=5), and
4. Rats fed chow with 5 DSS % and given 25 mg aminoguanidine hemisulfate/kg body weight/day by subcutaneous injection (n=4).

After 7 days on the DSS supplemented diet, the rats were anesthetized for assessment of vascular permeability in the cecum and large bowel. Vascular permeability was quantified by injection of radiolabeled albumin as described below.

Assessment of vascular function

Regional vascular albumin permeation was quantified by use of an isotope dilution technique based on the injection of bovine serum albumin (BSA) labeled with 2 different iodine isotopes, $^{125}I$ and $^{131}I$ ((Pugliese et al., *Metabolism* 39: 690–697, 1990; Pugliese et al., *Diabetes* 39: 323–332, 1990; and Pugliese et al., *Diabetes* 39: 312–322, 1990). $^{125}I$-BSA was used to quantify vascular albumin filtration after 10 min. of tracer circulation while $^{131}I$-BSA served as a plasma volume marker for correction of $^{125}I$-BSA tissue activity for tracer contained within vessels. Purified monomer BSA (1 mg) was iodinated with 1 mCi of $^{131}I$ or $^{125}I$ by the iodogen, method as previously described (Pugliese et al., *Diabetes* 39: 323–332, 1990).

Rats were anesthetized with Inactin (Byk Gulden, Konstanz, FRG) (~100 mg/kg body weight injected i.p.), and core body temperature maintained at 37°±0.5° C. using heat lamps, a 37° C. surgical tray, and, a rectal temperature probe. The left femoral vein, left iliac artery, and right subclavian artery were cannulated with polyethylene tubing (0.58 mm i.d.) filled with heparinized saline (400 V heparin/ml). The femoral vein cannula was used for tracer injection and the subclavian artery cannula was connected to a pressure transducer for blood pressure monitoring. The left iliac artery was connected to a 1 ml syringe attached to a Harvard Model 940 constant withdrawal pump preset to withdraw at a constant rate of, 0.055 ml/min. The trachea was intubated and connected to a small rodent respirator for continuous ventilatory support.

At time 0, $^{125}I$-albumin was injected and the withdrawal pump was started simultaneously. Eight min. after time 0, $^{131}$I-BSA was injected, followed by the microspheres. At the 10 min mark, the heart was excised to stop all blood flow, the withdrawal pump was stopped simultaneously, and various tissues were sampled for gamma spectrometry.

All tissue samples and arterial plasma samples were weighed and then counted in a gamma spectrometer. A quantitative index of $^{125}$I-BSA tissue clearance was calculated as previously described in (Pugliese et al., Metabolism 39: 690–697, 1990; Pugliese et al., Diabetes 39: 323–332, 1990; and Pugliese et al., Diabetes 39: 312–322, 1990) and expressed as µg plasma/g tissue wet weight/min. Briefly, $^{125}$I-BSA tissue activity was corrected for tracer contained within the tissue vasculature by multiplying $^{125}$I-BSA activity in the tissue by the ratio of $^{125}$I-BSA/$^{131}$I-BSA activities in the arterial plasma sample obtained at the end of the test. The vascular-corrected $^{125}$I-BSA tissue activity was divided by the time-averaged $^{125}$I-BSA plasma activity (obtained from a well mixed sample of plasma taken from the withdrawal syringe) and by the tracer circulation time (10 min) and then normalized per g tissue wet weight.

RESULTS

The vascular permeability changes induced by 5% DSS and the effects of aminoguanidine on them are summarized in Table 5. Vascular leakage was increased approximately 2 fold by 5% DSS in the cecum and in all portions of the colon. These increases were markedly attenuated in the cecum, proximal colon, and mid-colon by oral or subcutaneous aminoguanidine. The effects of aminoguanidine on vascular leakage of albumin in the distal colon were less impressive, although in animals given aminoguanidine by injection, leakage was substantially reduced ($p=0.065$). The reason oral aminoguanidine was less effective on permeability changes in the distal colon may be due to absorption of the drug in the proximal segments of bowel with insufficient amounts remaining to impact on leakage in the distal colon.

TABLE 5

Effects of aminoguanidine[a] on vascular leakage into large bowel in rats given 5% DSS[b] in the diet for 7 days

|  | Cecum | Proximal colon | Mid-colon | Distal colon |
| --- | --- | --- | --- | --- |
| Control(n = 9) | 218 ± 45[c] | 220 ± 47 | 247 ± 64 | 264 ± 35 |
| 5% DSS(n = 8) | 458 ± 68[d] | 501 ± 107[d] | 464 ± 98[d] | 562 ± 198[d] |
| +Ag Oral (n = 5) | 281 ± 89[e] | 249 ± 94[e] | 269 ± 78[e] | 523 ± 237 |
| +Ag Injection (n = 4) | 274 ± 63[e] | 222 ± 87[e] | 209 ± 55[e] | 319 ± 88 |

[a]25 mg/kg body weight per day in drinking water (oral) or by subcutaneous injection
[b]dextran sodium sulfate, (mol. wt. = 40,000–50,000)
[c]mean ± SD of albumin permeation expressed as µg plasma/g wet wt/min
[d]significantly different from control: $p<0.01$
[e]significantly different from 5% DSS: $p<0.01$ These results show that aminoguanidine given orally or by subcutaneous injection is efficacious in attenuating vascular damage in an animal model of inflammatory bowel disease. Since increased vascular leakage is a characteristic feature of acute and chronic inflammation and contributes to the diarrhea associated with the disease, these findings support the use of aminoguanidine in the treatment of inflammatory bowel disease in human subjects.

As noted above, it is possible that drug absorption occurred in the proximal bowel segments such that insufficient mounts remained in the distal colon. Under such circumstances, it might be desirable to utilize a sustained or delayed release formulation or an intrarectal route of administration in order to effectively treat the distal colon. Such sustained or delayed release or intrarectal formulations are well known in the art and can be prepared by the skilled artison with no more than routine experimentation (See for example, Remington's Pharmaceutical Sciences, Ed. Arthur Osol. 16th ed., 1980, Mack Publishing Co., Easton, Pa. which is incorporated by reference).

The inhibitors of nitric oxide formation described herein can be used for administration to warm blooded mammals by conventional means, preferably in formulations with pharmaceutically acceptable diluents and carriers. It will be understood that pharmaceutically acceptable salts of these compounds, e.g., the HCl, $HCO_3$ and sulfate salts, can also be administered to the host in accordance with the method of the invention.

The amount of the active inhibitor to be administered must be an effective amount, that is, an amount which is medically beneficial but does not present toxic effects which overweigh the advantages which accompany its use. It would be expected that the adult human daily dosage would normally range upward from about one milligram per kilo of body weight of the drug. Suitable routes of administration include, where appropriate, topical delivery via salves, ointments and solutions; or locally through suppositories, pessaries, and the like; orally in the form of capsules, tablets, syrups, elixirs and the like; intrarectal administration such as in the form of a suppository; and parenteral administration, e.g., intravenously, intraperitoneally or subcutaneously. Intravenous administration of the drug in aqueous solution such as physiologic saline is illustrative. Appropriate formulations of the drug in pharmaceutically acceptable diluents and carriers in therapeutic dosage form can be prepared by reference to general texts in the field such as, for example, Remington's Pharmaceutical Sciences, supra.

In embodiments of this invention in which the inhibitors of nitric oxide formation are administered topically or locally, the inflammatory disease or condition thereby treated includes but is not limited to uveitis and conjunctivitis; acute and chronic vaginitis; arthritis; insect bites; burns (thermal, chemical, and electrical); sunburn; acute and delayed hypersensitivity; skin conditions such as psoriasis, whether acute or chronic; eczema; contact dermatitis; poison ivy; poison oak; and poison sumac.

In embodiments in which the inhibitors of nitric oxide formation are administered orally, the inflammatory disease or condition thereby treated includes but is not limited to uveitis and conjunctivitis; acute and chronic gastroenteritis and colitis; arthritis; acute and chronic cystiris and urethritis; stroke; myocardial infarcts; myocarditis and pericarditis; and inflammatory bowel disease.

In embodiments in which the inhibitors of nitric oxide formation are administered parenterally, the inflammatory disease or condition thereby treated includes but is not limited to uveitis and conjuntivitis as well as any and all acute and chronic infections (bacterial and fungal, including diphtheria and pertussis); acute and chronic serositis (pericarditis, peritonitis, synovitis, pleuritis and tendinitis); uremic pericarditis; acute and chronic cholecystitis; meningitis; encephalitis; arthritis; graft vs. host disease; pernicious anemia; Type I diabetes mellitus; rheumatoid arthritis; multiple sclerosis; transplant rejection; inflammation due to toxic shock or trauma; adult respiratory distress syndrome; inflammatory bowel disease; stroke; myocardial infarction and myocarditis; and reperfusion injury.

Various other examples will be apparent to the person skilled in the art after reading the present disclosure without departing from the spirit and scope of the invention. It is intended that all such examples be included within the scope of the appended claims.

What is claimed is:

1. A method of inhibiting nitric oxide production in a warm blooded mammal afflicted with inflammatory bowel disease, said method comprising administering a nitric oxide inhibitory effective amount of aminoguanidine.

2. The method according to claim 1 wherein aminoguanidine is administered orally.

3. The method according to claim 2 wherein aminoguanidine. is administered in a pharmaceutically acceptable formulation.

4. The method according to claim 3 wherein aminoguanidine is in a sustained release or delayed release formulation.

5. The method according to claim 1 wherein aminoguanidine is administered intrarectally.

6. The method according to claim 5 wherein aminoguanidine is administered in a pharmaceutically acceptable formulation.

7. The method according to claim 1 wherein aminoguanidine is administered parenterally.

8. The method according to claim 7 wherein aminoguanidine is administered intravenously or subcutaneously.

9. The method according to claim 8 wherein aminoguanidine is administered in a pharmaceutically acceptable formulation.

* * * * *